United States Patent [19]

Becker et al.

[11] Patent Number: 5,260,303
[45] Date of Patent: Nov. 9, 1993

[54] IMIDAZOPYRIDINES AS SEROTONERGIC 5-HT$_3$ ANTAGONISTS

[75] Inventors: Daniel P. Becker, Glenview; Daniel L. Flynn, Mundelein; Alan E. Moormann, Skokie; Roger Nosal, Buffalo Grove; Clara I. Villamil, Glenview, all of Ill.

[73] Assignee: G. D. Searle & Co., Chicago, Ill.

[21] Appl. No.: 666,113

[22] Filed: Mar. 7, 1991

[51] Int. Cl.$^5$ .................. C07D 453/06; A61K 31/435
[52] U.S. Cl. ..................................... 514/300; 546/121
[58] Field of Search ........................ 546/121; 514/300

[56] References Cited

U.S. PATENT DOCUMENTS

| | | | |
|---|---|---|---|
| 4,273,778 | 6/1981 | Hadley et al. | 424/265 |
| 4,336,259 | 6/1982 | Hadley et al. | 424/265 |
| 4,797,387 | 1/1989 | King | 514/212 |
| 4,797,406 | 1/1989 | Richardson et al. | 514/299 |
| 4,816,453 | 3/1989 | Watts | 514/217 |

FOREIGN PATENT DOCUMENTS

| | | |
|---|---|---|
| 12496/83 | 9/1983 | Australia . |
| 6712187 | 7/1987 | Australia . |
| 094742 | 11/1982 | European Pat. Off. . |
| 0076592 | 4/1983 | European Pat. Off. . |
| 0189002 | 7/1986 | European Pat. Off. . |
| 0201165 | 11/1986 | European Pat. Off. . |
| 0220011 | 4/1987 | European Pat. Off. . |
| 0230718 | 6/1987 | European Pat. Off. . |
| 0254584 | 1/1988 | European Pat. Off. . |
| 0289170 | 11/1988 | European Pat. Off. . |
| 0315390 | 5/1989 | European Pat. Off. . |
| 0323077 | 7/1989 | European Pat. Off. . |
| 258674 | 10/1989 | Japan . |
| 2152049 | 7/1985 | United Kingdom . |
| 2166726 | 5/1986 | United Kingdom . |
| 2169292 | 7/1986 | United Kingdom . |

OTHER PUBLICATIONS

Chemical Abstracts Service vol. 110: 192817f (1989) (Abstract of EP 289170).
Chemical Abstracts Service vol. 112: 178986v (1990) (Abstract of JP 01,258,674).
Fludzinski et al., Indazoles as Indole Bioesters J. Med. Chem. vol. 30 No. 9 1535-7 Apr. 1987.

Primary Examiner—Marianne M. Cintins
Assistant Examiner—Catherine Scalzo
Attorney, Agent, or Firm—Cynthia S. Kovacevic; Roger A. Williams

[57] ABSTRACT

The imidazopyridines compounds of the present invention are serotonergic 5-HT$_3$ antagonists. As such they are useful for the treatment of humans and animals wherein antagonism of 5-HT$_3$ receptors is beneficial. Therapy is indicated for, but not limited to, the treatment of anxiety, psychoses, depression (especially depression accompanied by anxiety), cognitive disorders, substance abuse dependence and withdrawal, gastrointestinal motility disturbancies (including esophageal reflux, dyspepsia, gastric stasis, irritable bowel syndrome), emesis caused by chemotherapeutic agents, and visceral pain. Additionally, the compounds of the present invention may find utility as enhancers of nasal absorption of bioactive compounds.

24 Claims, No Drawings

IMIDAZOPYRIDINES AS SEROTONERGIC 5-HT₃ ANTAGONISTS

BACKGROUND OF THE INVENTION

The invention herein is directed to compounds and a method of treating gastrointestinal motility disorders of a mammal by administering to the mammal in need thereof a therapeutically effective amount of a compound disclosed herein or a pharmaceutically acceptable salt thereof. The method can be practiced to treat gastrointestinal motility disorders such as gastroesophageal reflux, diseases characterized by delayed gastric emptying, ileus, irritable bowel syndrome, and the like. The compounds of the invention are serotonergic 5-HT₃ antagonists and as such are useful for the treatment of conditions, for example, such as anxiety, psychoses and depression.

There are classes of compounds known for the treatment of such disorders. For example, azatetracycle compounds are disclosed in co-pending U.S. patent application Ser. No. 07/515,391 filed Apr. 27, 1990, and N-Azabicyclo [3.3.0] octane amides of aromatic acids are disclosed in co-pending application Ser. No. 07/406,205 filed Sep. 11, 1989.

Aza-adamantyl compounds are disclosed in U.S. Pat. No. 4,816,453 and are mentioned generically n U.K. Patent 2,152,049A and European application 0189002A2.

Azabicyclic nonanes are disclosed in European Patent application 0094742A2. Additional azabicyclic compounds are disclosed in U.S. Pat. Nos. 4,797,387 and 4,797,406.

Benzamides have been known as 5-HT₃ antagonists and as compounds possessing gastrointestinal motility-enhancing properties. Benzamides of the following formula:

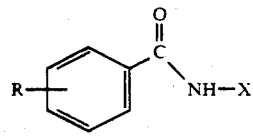

compounds wherein X can be an azabicycloalkane moiety and which exhibit gastrointestinal motility enhancing and/or 5-HT₃ antagonist properties are disclosed in EP 0094742A2 and in U.S. Pat. No. 4,797,406. In addition, UK Patent 2,152,049 discloses that certain benzamide derivatives exhibit serotonin M antagonistic activity.

Indoleamides of the following formula have also been described as possessing gastrointestinal motility-enhancing and/or 5-HT₃ antagonist properties:

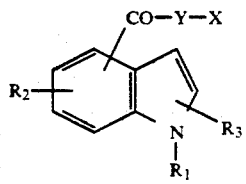

Compounds wherein X contains an aminergic side chain or an azabicycloalkane moiety are described in U.S. Pat. No. 4,797,406.

European patent publication number 0,230,718 discloses certain substituted benzamide derivatives, substituted with piperidinyl analogues as having gastrointestinal motility-enhancing and/or antiemetic activity and/or 5-HT₃ receptor antagonist activity.

SUMMARY OF THE INVENTION

The compounds of the present invention are serotonergic 5-HT₃ antagonists. As such they are useful for the treatment of humans and animals wherein antagonism of 5-HT₃ receptors is beneficial. Therapy is indicated for, but not limited to, the treatment of anxiety, psychoses, depression (especially depression accompanied by anxiety), cognitive disorders, substance abuse dependence and withdrawal, gastrointestinal motility disturbancies (including esophageal reflux, dyspepsia, gastric stasis, irritable bowel syndrome), emesis caused by chemotherapeutic agents, and visceral pain. Additionally, the compounds of the present invention may find utility as enhancers of nasal absorption of bioactive compounds.

The invention herein is directed to compounds of the formula

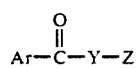

the stereoisomers and pharmaceutically acceptable salts thereof, wherein Ar represents a radical of the formula

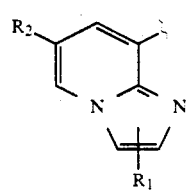

A

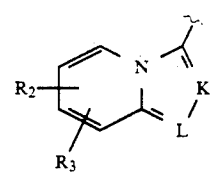

B

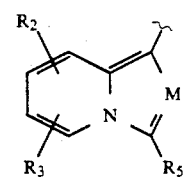

C

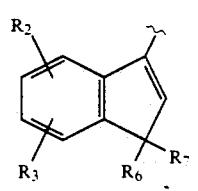

D

-continued

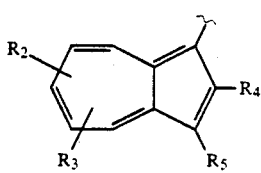
E

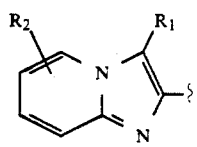
F

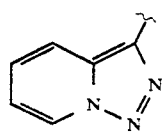
G

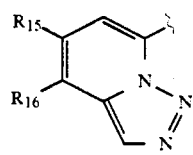
H

Wherein in group A $R_1$ is H, or $C_{1-6}$ alkyl, and $R_2$ is H, or halogen;

In group B, K is N or $CR_4$, L is N or $CR_5$, $R_2$ & $R_3$ are independently H or halogen, $R_4$ is H, or $C_{1-6}$ alkoxy and $R_5$ is H, halogen, $CF_3$, $C_{1-6}$ alkyl, $C_{1-6}$ alkoxy, $C_{1-6}$ alkylthio, $C_{1-6}$ alkylsulfonyl, $C_{1-6}$ alkylsulfinyl, $C_{1-7}$ acyl, cyano, $C_{1-6}$ alkoxycarbonyl, $C_{1-7}$ acylamino, hydroxy, nitro, amino, aminocarbonyl, or aminosulfonyl optionally N-substituted by one or two groups selected from $C_{1-6}$ alkyl, $C_{3-8}$ cycloalkyl, and $C_{3-8}$ cycloalkyl$C_{1-4}$alkyl or disubstituted by $C_4$ or $C_5$ polymethylene; phenyl or phenyl $C_{1-4}$ alkyl group optionally substituted in the phenyl ring by one or two of halogen, $C_{1-6}$ alkoxy or $C_{1-6}$ alkyl groups;

In group C, M is N or $CR_4$, $R_2$ & $R_3$ are independently H or halogen, $R_4$ is H or $C_{1-6}$ alkoxy and $R_5$ is H, halogen, $CF_3$, $C_{1-6}$ alkyl, $C_{1-6}$ alkoxy, $C_{1-6}$ alkylthio, $C_{1-6}$ alkylsulfonyl, $C_{1-6}$ alkylsulfinyl, $C_{1-7}$ acyl, cyano, $C_{1-6}$ alkoxycarbonyl, $C_{1-7}$ acylamino, hydroxy, nitro, amino, aminocarbonyl, or aminosulfonyl optionally N-substituted by one or two groups selected from $C_{1-6}$ alkyl, $C_{3-8}$ cycloalkyl, and $C_{3-8}$ cycloalkyl$C_{1-4}$alkyl or disubstituted by $C_4$ or $C_5$ polymethylene, phenyl or phenyl $C_{1-4}$ alkyl group optionally substituted in the phenyl ring by one or two of halogen, $C_{1-6}$ alkoxy or $C_{1-6}$ alkyl groups;

In group D one of $R_6$ and $R_7$ is $C_{1-6}$ alkyl and the other is $C_{1-6}$ alkyl, phenyl or phenyl $C_{1-4}$ alkyl optionally substituted in either phenyl ring by one or two of $C_{1-6}$ alkyl, $C_{1-6}$ alkoxy, or halogen, or $R_6$ & $R_7$ together are $C_{2-6}$ polymethylene or $C_{2-5}$ polymethylene interrupted by an —O— linkage, and $R_2$ & $R_3$ are independently H or halogen;

In group E, $R_4$ is H or $C_{1-6}$ alkoxy, $R_5$ is H or $C_{1-6}$ alkoxy, and $R_2$ is H, halogen, $CF_3$, $C_{1-6}$ alkyl, $C_{1-6}$ alkoxy, $C_{1-6}$ alkylthio, $C_{1-6}$ alkylsulfonyl, $C_{1-6}$ alkylsulfinyl, $C_{1-7}$ acyl, cyano, $C_{1-6}$ alkoxycarbonyl, $C_{1-7}$ acylamino, hydroxy, nitro, amino, aminocarbonyl, or aminosulfonyl, optionally N-substituted by one or two groups selected from $C_{1-6}$ alkyl, $C_{3-8}$ cycloalkyl, and $C_{3-8}$ cycloalkyl$C_{1-4}$alkyl or disubstituted by $C_4$ or $C_5$ polymethylene, phenyl or phenyl $C_{1-4}$ alkyl group optionally substituted in the phenyl ring by one or two of halogen, $C_{1-6}$ alkoxy or $C_{1-6}$ alkyl groups, and $R_2$ & $R_3$ are independently H or halogen;

In group F, $R_1$ is H or $C_{1-6}$ alkyl, and $R_2$ is H or halogen; and In group H $R_{15}$ & $R_{16}$ are independently H or —CH=CH—CH=CH—;

Y represents NH or O; and

Z represents a radical of the formula

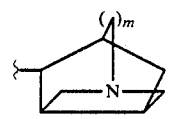
$Z_1$

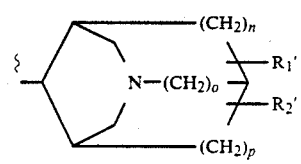
$Z_2$

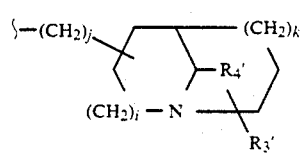
$Z_3$

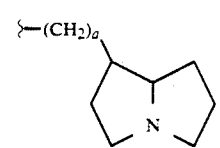
$Z_4$

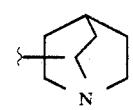
$Z_5$

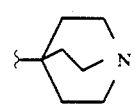
$Z_6$

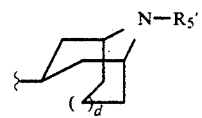
$Z_7$

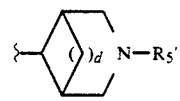
$Z_8$

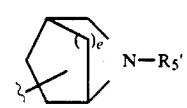
$Z_9$

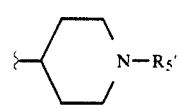
$Z_{10}$

-continued

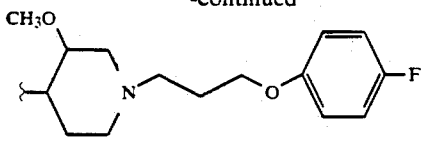
$Z_{11}$

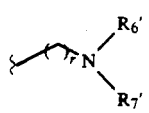
$Z_{12}$

Wherein in group $Z_1$ m is 1 or 2;

In group $Z_2$ n and p are independently 1 or 2 and o is 0, 1, or 2 such that $n+p+o \geq 3$, and $R'_1$ and $R'_2$ are independently H, $C_{1-6}$ alkyl, phenyl or phenyl-$C_{1-6}$ alkyl, which phenyl moieties may be substituted by $C_{1-6}$ alkyl, $C_{1-6}$ alkoxy, or halogen;

In group $Z_3$ k is 0 to 2, l is 0 to 3, j is 0 to 4, and one of $R'_3$ and $R'_4$ is H, $C_{1-6}$ alkyl, phenyl, or phenyl-$C_{1-3}$ alkyl, which phenyl moieties may be optionally substituted by $C_{1-6}$ alkyl, $C_{1-6}$ alkoxy, $CF_3$ or halogen, and the other of $R'_3$ and $R'_4$ is H or $C_{1-6}$ alkyl;

In group $Z_4$ a is 0 or 1;

In group $Z_7$ d is 0 or 1, and $R'_5$ is $C_{1-7}$ alkyl, $C_{3-8}$ cycloalkyl, $C_{3-8}$ cycloalkyl-$C_{1-2}$ alkyl, $C_{2-7}$ alkenyl, $C_{2-7}$ alkylenyl-$C_{1-4}$ alkyl, or phenyl-$C_{1-6}$ alkyl.

In group $Z_8$ d and $R'_5$ are as previously defined;

In group $Z_9$ e is 1 or 2, and $R'_5$ is as previously defined;

In group $Z_{10}$ $R'_5$ is as previously defined; and

In group $Z_{12}$ r is 1 to 4, $R'_6$ and $R'_7$ are independently $C_{1-6}$ alkyl, $C_{1-6}$ alkenyl, or $C_{1-6}$ alkynyl or together form —(CH2)s—, wherein s is 3–7 and one of the $CH_2$ units may optionally be replaced by —O—, or $NR'_8$, wherein $R'_8$ is H or $C_{1-6}$ alkyl;

with the proviso that when Ar is group B, C, D or E, then Z cannot be $Z_5$, $Z_7$ or $Z_9$.

The term "cycloalkyl" embraces cyclic radicals having three to about ten ring carbon atoms, preferably three to about six carbon atoms, such as cyclopropyl and cyclobutyl. The term "haloalkyl" embraces radicals wherein any one or more of the alkyl carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two bromo atoms, such as a dibromomethyl group, or two chloro atoms, such as a dichloromethyl group, or one bromo atom and one chloro atom, such as a bromochloromethyl group. Examples of a polyhaloalkyl are trifluoromethyl, 2,2,2-trifluoroethyl, perfluoroethyl and 2,2,3,3-tetrafluoropropyl groups. The terms "alkoxy" and "alkoxyalkyl" embrace linear or branched oxy-containing radicals each having alkyl portions of one to about ten carbon atoms, such as methoxy group.

Specific examples of alkyl groups are methyl, ethyl, n-propyl, isopropyl, n-butyl, sec-butyl, iso-butyl, tert-butyl, n-pentyl, iso-pentyl, methyl-butyl, dimethylbutyl and neopentyl. Typical alkenyl and alkynyl groups may have one unsaturated bond, such as an allyl group, or may have a plurality or unsaturated bonds, with such plurality of bonds either adjacent, such as allene-type structures, or in conjugation, or separated by several saturated carbons.

Included within the family of compounds of the described are the tautomeric forms of the described compounds, isomeric forms including diastereoisomers and individual enantiomers, and the pharmaceutically-acceptable salts thereof. The term "pharmaceutically-acceptable salts" embraces salts commonly used to form alkali metal salts and to form addition salts of free acids or free bases. Since the compounds contain basic nitrogen atoms, such salts are typically acid addition salts. The phrase "pharmaceutically-acceptable salts" is intended to embrace alkyl quaternary ammonium salts and n-oxides. The nature of the salt is not critical, provided that it is pharmaceutically acceptable, and acids which may be employed to form such salts are, of course, well known to those skilled in this art. Examples of acids which may be employed to form pharmaceutically acceptable acid addition salts include such inorganic acids as hydrochloric acid, sulfuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. All of these salts may be prepared by conventional means by reacting, for example, the appropriate acid or base with the corresponding compound of the invention.

The compounds that are the subject of the invention herein can be prepared according to the following reaction schemes.

SCHEME 1

The preparation of compounds of formula I wherein the Ar group is A is shown in Scheme I. Compounds of formula I A are prepared starting from commercially available 2-aminonicotinic acid 1. Chloroacetaldehyde is reacted with 1 at elevated temperature in an alcoholic solvent (preferably EtOH at reflux) to afford compound 2A, which is converted to the acid chloride by conventional methods (preferably thionyl chloride/-chloroform/dimethylformamide at reflux). This acid chloride 2B is then reacted with the appropriate amine 3 in the presence of a tertiary amine (preferably triethylamine) in a polar organic solvent (preferably dimethylformamide) to afford the desired compounds of formula IA. Alternatively, the imidazopyridine carboxylic acid 2A is reacted with the amine 3 using other acid-activating reagents (dicyclohexylcarbodiimide, iso-butylchloroformate, carbonyldiimidazole (CDI), etc.; preferably CDI in dimethylformamide at room temperature) to afford compounds of formula 1A.

Ring halogenated analogs of formula IA' are prepared according to scheme I. 2-Aminonicotinic acid 1 is converted to its methyl ester by conventional means. Treatment of this ester with halogenating reagents (NBS, NCS, Cl2, t-butylhypochlorite; preferably t-butylhypochorite/methanol/room temperature) gives rise to the ring halogenated intermediate 4, which is converted to the imidazopyridine carboxylic acid ester 5A using conditions described above for the preparation of 2A. The corresponding imidazopyridine carboxylic acid 5 B is converted to compounds of formula IA' using reagents and conditions described above for the preparation of I A from 2A.

SCHEME 2

The preparation of compounds of formulae IB, IC, ID, and IE are shown in scheme 2. In each case, the known acids 10 [EP 0254584A2, J. Medicinal Chemistry (1990), 33, 1924], 11 [EP 0289170A2, J. Medicinal Chemistry (1990), 33, 1924], 12 & 13 [EP 0289170A2, J. Medicinal Chemistry (1990), 33, 1929] are reacted with the appropriate amine or alcohol under conditions analogous to those described for scheme 1 or as described in EP 0254584A2 and EP 0289170A2.

SCHEME 3

The preparation of compounds of formula IF are shown in scheme 3. 2-Aminopyridine 14 is reacted with ethyl bromopyruvate 15 in an alcoholic solvent (preferably ethanol) to afford the imidazopyridine carboxylic acid ester 16A. Hydrolysis of the ester to the acid 16B occurs under conventional acid-catalyzed conditions. Conversion of 16B to amides and ester of formula IF is affected by employing one of a number of acid-activating reagents as sited above [preferably carbonyl-diimidazole (CDI) in dimethylformamide at room temperature].

SCHEME 4

The preparation of compounds of formulae I-G and I-H are shown in Scheme 4. The known triazole aldehyde 17 [G. Jones et al., J. Chemical Society Perkin I (1981), 78] is oxidized by use of chromium trioxide/sulfuric acid or other conventional oxidizing agents to afford the triazole carboxylic acid 18. Coupling of 18 with the appropriate amine or alcohol 3 using conditions sited above [preferably CDI in dimethylformamide at room temperature] affords the desired triazoles of formula 1-G.

For preparation of compounds of formula I-H, the known lithiated compound 19 [B. Abarca et al, J. Chemical Society Perkin I (1985), 1897] is quenched with carbon dioxide or alkylhaloformate to afford 20B and 20A, respectively. 20A is converted to the acid 20B by conventional acid-catalyzed hydrolysis. Coupling of 20B with the appropriate amine or alcohol 3 is affected by using the conditions sited above [preferably CDI in dimethylformamide at room temperature] to afford the desired I-H. Alternatively, the appropriate amine 3 is converted to its carbamoyl halide 21 (Q=Cl, Br) or isocyanate 22. The lithiated species 19 is directly quenched with 21 or 22 to directly afford I-H (Y=NH).

These examples, as well as all examples herein, are given by way of illustration only and are not to be construed as limiting the invention, either in spirit or scope, as many modifications, both in materials and methods, will be apparent from this disclosure to those skilled in the art. In these examples, temperatures are given in degrees Celsius (°C.) and quantities of materials in grams and milliliters unless otherwise noted.

Scheme I: Preparation of Imidazopyridines (Ar group=A)

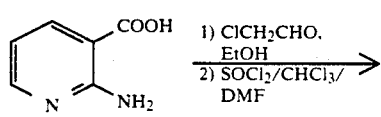

-continued

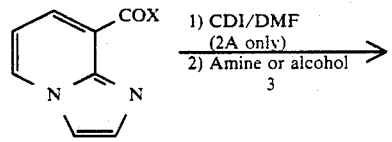

2A, X = OH
2B, X = Cl

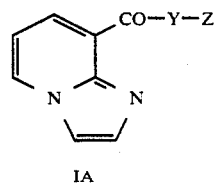

IA

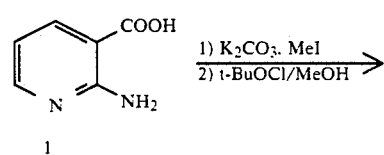

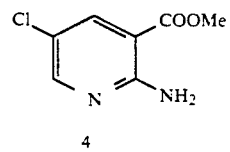

4

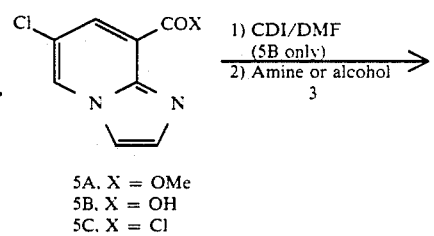

5A, X = OMe
5B, X = OH
5C, X = Cl

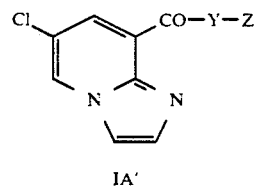

IA'

Scheme 2: Preparation of Compounds of Formulae IB, IC, ID and IE

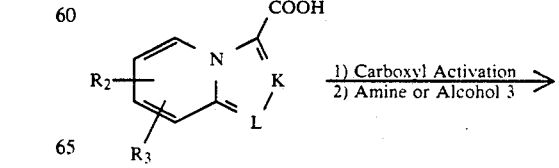

10

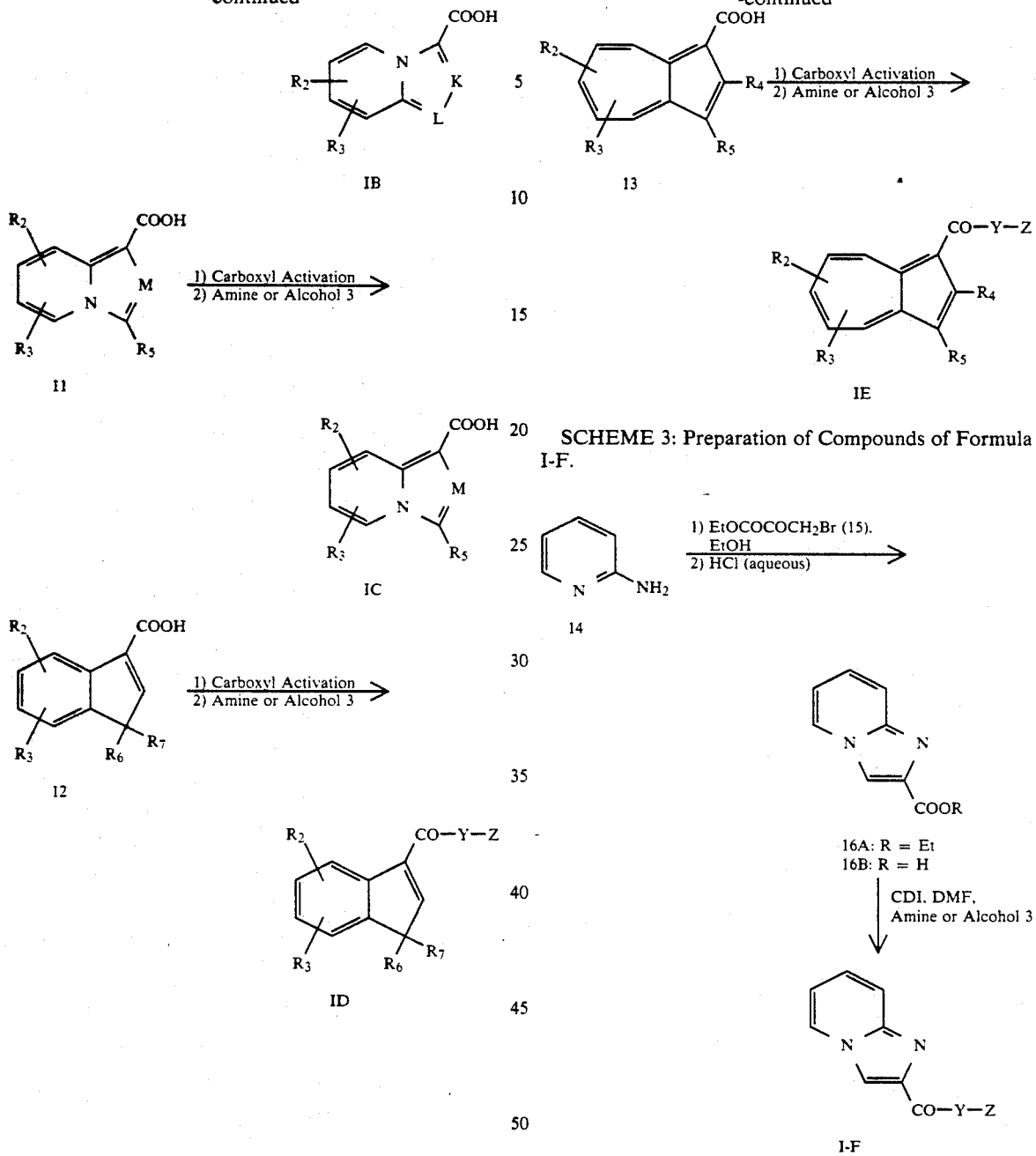
SCHEME 3: Preparation of Compounds of Formula I-F.
SCHEME 4: PREPARATION OF COMPOUNDS OF FORMULAE I-G AND I-H
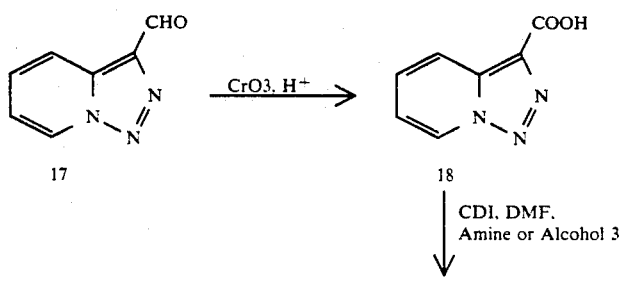

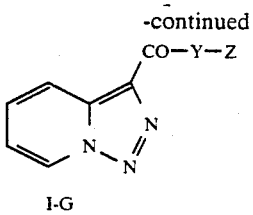

I-G

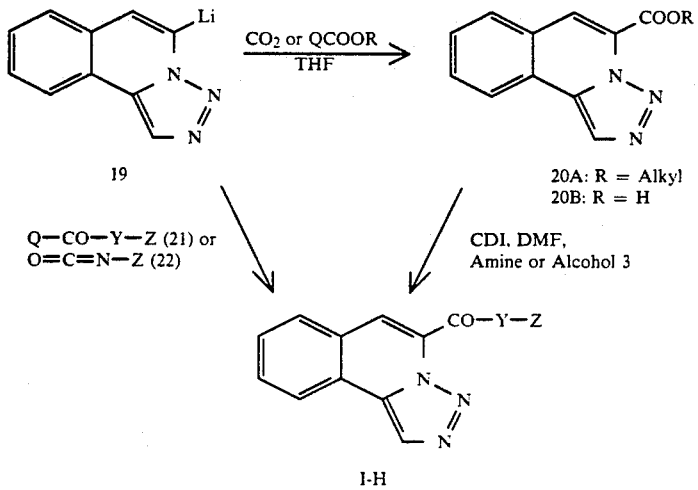

I-H

EXAMPLE A (Methyl 2-aminonicotinate)

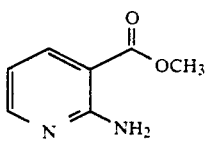

Procedure

The 2-aminonicotinic acid (5.0 g, 0.0362 mol) and $K_2CO_3$ (5.0 g, 0.0362 mol) were suspended in 50 ml of DMF and heated to reflux. Almost complete solution occurred. The mixture was cooled to 25° C. and the $CH_3I$ (5.1 g/2.2 ml, 0.0362 mol) was added and the mixture was stirred 18 hours. The mixture was filtered and concentrated. The residue was placed on a bed of silica and eluted with 5%/ $EtOH/CH_2Cl_2/1/10\%$ $NH_4OH$. The fractions containing the product were combined and concentrated. The residue was suspended in $Et_2O$, filtered and washed with $Et_2O$ to yield 3.2 g (58%) the title compound.

| Elements | Calc | Found | |
|---|---|---|---|
| Carbon | 55.26 | 54.90 | $C_7H_8N_2O_2$ |
| Hydrogen | 5.30 | 5.36 | |
| Nitrogen | 18.41 | 18.26 | MW 152.15 |

EXAMPLE B (Methyl 2-amino-5-chloronicotinate)

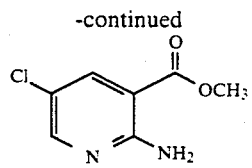

Procedure

The compound of example A (800 mg, 0.00525 mol) was dissolved in MeOH (15 ml) and HCl gas was passed over the solution until the solution was acidic (pH 2). The solution was concentrated and the residue redissolved in MeOH (15 ml). The t-butylhypochlorite (570 mg, 0.00525 mol) was added and the reaction mixture stirred until the yellow color dissipated. Additional t-butylhypochlorite was added until tlc (5% $EtOH/CH_2Cl_2/1/10\%$ $NH_4OH$) indicated that the starting material was consumed.

The reaction mixture was concentrated and the residue dissolved in $CH_2Cl_2$. The organics were washed with 5% $NaHCO_3$ then 5% sodium thiosulfate. The organic layer was dried over $MgSO_4$ and concentrated to afford a solid. The solid was suspended in 1:1 $CH_2Cl_2$/hexane, filtered, washed with hexane and suction dried to yield 250 mg (26%) of the title compound m.p. 139°-40° C.

| Elements | Calc | Found | |
|---|---|---|---|
| Carbon | 45.60 | 44.72 | $C_7H_7ClN_2O_2$ |
| Hydrogen | 3.78 | 3.75 | |
| Nitrogen | 15.01 | 15.00 | MW 186.60 |
| Chlorine | 19.00 | 19.20 | |

EXAMPLE C (6-Chloroimidazo[1,2-a]pyridine-8-carboxylic acid, monohydrochloride)

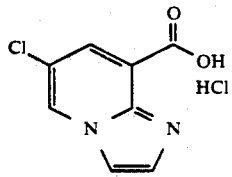

Procedure

The compound of example B (1.2 g, 0.0063 mol) and chloroacetaldehyde [45% aqueous solution (930 mg, 0.007 mol)] was heated to reflux in EtOH until tlc (5% EtOH/CH$_2$Cl$_2$/1/10% NH$_4$OH) indicated that the reaction was complete. The solution was concentrated and the residue was suspended in acetone, filtered, washed with acetone, and air dried to yield 1.3 g (77%) of the methyl ester of the title compound m.p. 148°–150° C. (resolidify) 235°–238° C. (decomp).

| Elements | Calc | Found | |
|---|---|---|---|
| Carbon | 40.50 | 40.58 | C$_9$H$_7$ClN$_2$O$_2$*1.05 HCl*1.0H$_2$O |
| Hydrogen | 3.80 | 3.82 | |
| Nitrogen | 10.50 | 10.53 | MW 266.92 |
| Chlorine | 27.23 | 27.43 | |

The methyl ester was heated to reflux in 15 ml of con HCl until tlc (5% EtOH/CH$_2$Cl$_2$/1/10% NH$_4$OH) indicated that the starting material was consumed. Concentration gave a residue which was suspended in acetone, filtered and dried to afford 1.15 g (99%) of the title compound: softens 275° C.; m.p. 279°–281° C. (decomp).

| Elements | Calc | Found | |
|---|---|---|---|
| Carbon | 41.23 | 40.99 | C$_8$H$_5$ClN$_2$O$_2$*HCl |
| Hydrogen | 2.60 | 2.53 | |
| Nitrogen | 12.02 | 11.95 | MW 233.05 |
| Chlorine | 30.42 | 30.52 | |

EXAMPLE D (Imidazo[1,2-a]pyridine-8-carboxylic acid, monohydrochloride)

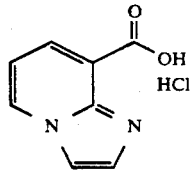

Procedure

Using 2-aminonicotinic acid (14.1 g, 0.102 mol) and chloroacetaldehyde [45% aqueous solution (8.6 g, 0.11 mol)], the same procedure as described above in example C was used. After workup 17.5 g (88%) of the title compound, m.p. 299°–300° C. (decomp), was isolated.

| Elements | Calc | Found | |
|---|---|---|---|
| Carbon | 48.38 | 48.16 | C$_9$H$_7$ClN$_2$O$_2$*1 HCl |
| Hydrogen | 3.55 | 3.59 | |
| Nitrogen | 14.10 | 13.95 | MW 198.61 |

| Elements | Calc | Found |
|---|---|---|
| Chlorine | 17.85 | 17.50 |

EXAMPLE E (Imidazo[1,2-a]pyridine-2-carboxylic acid monohydrochloride)

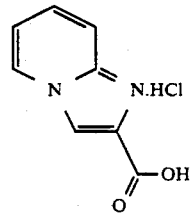

Procedure 2-aminopyridine (25.0 g, 0.128 mol) and ethyl bromopyruvate (12.0 g, 0.128 mol) were heated to reflux in EtOH (225 ml). The reaction mixture was concentrated and the residue partitioned between dilute K$_2$CO$_3$ and CH$_2$Cl$_2$. The organic layer was passed through a small bed of silica, eluting with 0.5% EtOH/CH$_2$Cl$_2$. The product eluted at the solvent front and this fraction was concentrated. The solid residue was suspended in Et$_2$O then filtered to yield 10.9 g (44%) of the ethyl ester of the title compound.

| Elements | Calc | Found | |
|---|---|---|---|
| Carbon | 62.56 | 62.79 | C$_{10}$H$_{10}$N$_2$O$_2$*.1 H$_2$O |
| Hydrogen | 5.35 | 5.33 | |
| Nitrogen | 14.59 | 14.62 | MW 192.00 |

The ethyl ester (5.0 g, 0.0256 moles) was refluxed in 50 ml of con HCl until tlc (5% EtOH/CH$_2$Cl$_2$/1/10% NH$_4$OH) indicated that the starting material was consumed. Concentration gave a residue which was suspended in acetone, filtered and dried to afford 5.2 g (95%) of the title compound.

| Elements | Calc | Found | |
|---|---|---|---|
| Carbon | 44.36 | 44.23 | C$_8$H$_6$N$_2$O$_2$*HCl |
| Hydrogen | 4.19 | 4.17 | |
| Nitrogen | 12.93 | 12.77 | MW 216.62 |
| Chlorine | 16.37 | 16.45 | |

EXAMPLE 1

(endo-N-(1-Azabicyclo[3.3.1]nonan-4-yl)-6-chloroimidazo[1,2-a]pyridine-8-carboxamide, dihydrochloride)

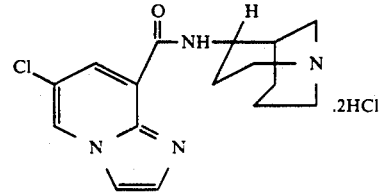

Procedure

15

The compound of example C (1.1 g, 0.0047 mol) was suspended in CHCl₃/DMF (25 ml/3 drops). SOCl₂ (560 mg/0.338 ml, 0.0047 mol) was added and the mixture was heated to reflux with additional SOCl₂ added until tlc (5% EtOH/CH₂Cl₂/1/10% NH₄OH) indicated that the starting material was consumed. The mixture was concentrated in vacuo, azeotroping once with toluene.

To the residue, dissolved in DMF (15 ml) and cooled in an ice bath, was added Et₃N (1.19 g/1.64 ml, 0.0118 mol) followed by endo-4-amino-1-azabicyclo[3.3.1]nonane (649 mg, 0.0047 mol) dissolved in 5 ml of DMF. The mixture was warmed to room temperature and stirred for 4 hours. Tlc (10% EtOH/CH₂Cl₂/1/10% NH₄OH) on basic alumnia indicated that the acid chloride was consumed. Concentration afforded a residue which was chromatographed on basic alumnia eluting with 1% EtOH/CH₂Cl₂/1/10% NH₄OH. The fractions containing the product were combined and concentrated in vacuo.

The residue was converted to the hydrochloride salt by dissolving in iPrOH and passing HCl gas over the solution. The solid was filtered, washed with iPrOH and dried in a vacuum desicator to yield 445 mg (20%) of the title compound, softens 230° C.; m.p. 264°–266° C. (decomp).

| Elements | Calc | Found | |
|---|---|---|---|
| Carbon | 43.72 | 43.57 | C₁₆H₁₉ClN₄O*2.6 HCl*2.0 H₂O*0.45 iPrOH |
| Hydrogen | 6.17 | 5.80 | |
| Nitrogen | 11.58 | 11.40 | MW 476.68 |
| Chlorine | 26.77 | 26.52 | |

EXAMPLE 2

(endo-N-(1-Azabicyclo[3.3.1]nonan-4-yl)imidazo[1,2-a]pyridine-8-carboxamide, dihydrochloride)

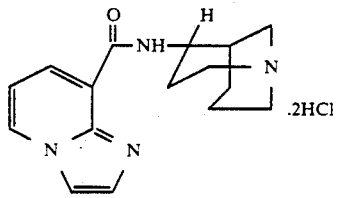

Procedure

Employing the compound of example D (1.4 g, 0.0071 mol), SOCl₂ (2.3 g/1.4 ml, 0.02 mol), endo-4-amino-1-azabicyclo[3.3.1]nonane (1.0 g, 0.00713 mol),

16

-continued

| Elements | Calc | Found | |
|---|---|---|---|
| Nitrogen | 15.30 | 15.12 | MW 366.24 |
| Chlorine | 19.36 | 19.26 | |

EXAMPLE 3

(endo-N-(8-Methyl-8-azabicyclo[3.2.1]octan-3-yl)-6-chloroimidazo[1,2-a]pyridine-8-carboxamide, dihydrochloride)

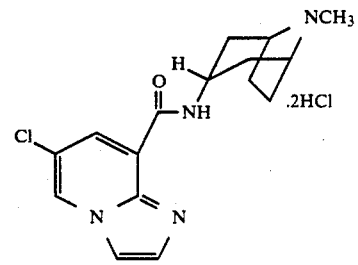

Procedure

The compound of example C (233 mg, 0.001 mol) and 1,1'-carbonyldiimidazole (241 mg, 0.0015 moles) were suspended in DMF (5 ml) and the mixture was stirred until solution occured (three hours). Endo-N-8-methyl-8-azabicyclo[3.2.1]-octane-3-amine [produced in accordance with the procedure in J. Am. Chem. Soc. 79, 4194(1957)] was added and the mixture was stirred for 18 hours. Tlc (30% EtOH/CH₂Cl₂/1/10% NH₄OH) indicated that the reaction was complete. Concentration afforded a residue which was purified by radial chromatography [(2 mm plate), gradient elution with 25% to 75% i-PrOH/CH₂Cl₂/1/10% NH₄OH]. Three components were collected. The desired was found in the third-eluted component. Concentration afforded a residue which was converted to the hydrochloride salt by dissolving in iPrOH and passing HCl gas over the solution. The solid was filtered, washed with iPrOH and dried in a vacuum desicator to yield 113 mg (25%) of the title compound.

| Elements | Calc | Found | |
|---|---|---|---|
| Carbon | 48.17 | 47.77 | C₁₆H₁₉ClN₄O*2 HCl*H₂O*0.75 iPrOH |
| Hydrogen | 6.43 | 6.36 | |
| Nitrogen | 12.32 | 11.98 | MW 454.82 |
| Chlorine | 23.38 | 23.18 | | and Et₃N (2.5 g/3.84 ml, 0.0249 mo) dissolved in CHCl₃/DMF (25 ml/3 drops), the same procedure as described in example 1 was used. After workup 121 mg (5%) of the title compound was isolated.

| Elements | Calc | Found | |
|---|---|---|---|
| Carbon | 51.65 | 51.43 | C₁₅H₂₀N₄O*2 HCl*½H₂O*0.25 iPrOH |
| Hydrogen | 6.79 | 6.38 | |

EXAMPLE 4

(endo-N-(8-methyl-8-azabicyclo[3.2.1]octan-3-yl)imidazo[1,2-a]pyridine-8-carboxamide, hydrochloride)

17

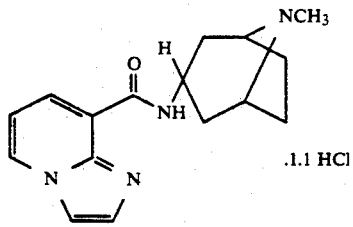

.1.1 HCl

Procedure

The compound of example D (200 mg, 0.00101 mol) and 1,1'-carbonyldiimidazole (164 mg, 0.00101 mol) were suspended in the DMF (2 ml) and the mixture was stirred until solution occured (2.5 hours). Endo-N-8-methyl-8-azabicyclo[3.2.1]-octane-3-amine was added and the mixture was stirred for 48 hours. The mixture was concentrated to one half the original volume and EtOAc (2 ml) was added. The solid was filtered to afford (126 mg, 39%) the title compound.

| Elements | Calc | Found | | |
|---|---|---|---|---|
| Carbon | 58.26 | 58.00 | $C_{16}H_{20}N_4O*1.1$ HCl*0.3H$_2$O | |
| Hydrogen | 6.63 | 6.65 | | |
| Nitrogen | 16.99 | 17.02 | MW 329.67 | |
| Chlorine | 11.82 | 11.90 | | |

MS calcd for $C_{16}H_{20}N_4O$ 284.1637; found 284.1640.

EXAMPLE 5

(exo-N-(8-methyl-8-azabicyclo[3.2.1]octan-3-yl)imidazo[1,2-a]pyridine-8-carboxamide, hydrochloride)

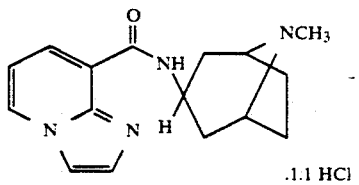

.1.1 HCl

Procedure

The compound of example D (200 mg, 0.00101 mol) and 1,1'-carbonyldiimidazole (164 mg, 0.00101 mol) were suspended in DMF (2 ml) and the mixture was stirred until solution occured (2.5 hours). Exo-N-8-methyl-8-azabicyclo[3.2.1]octane-3-amine [prepared in accordance with the procedure in Berichte 31, 1202(1898)] was added to the mixture and the resulting suspension was stirred for 4 days. EtOAc was added to the mixture and the solid filtered to afford (282 mg, 76%) the title compound.

| Elements | Calc | Found | |
|---|---|---|---|
| Carbon | 59.23 | 59.30 | $C_{16}H_{20}N_4O*1.1$ HCl |
| Hydrogen | 6.56 | 6.71 | |
| Nitrogen | 17.24 | 17.33 | MW 324.47 |

18

| Elements | Calc | Found |
|---|---|---|
| Chlorine | 12.02 | 11.85 |

MS calcd for $C_{16}H_{20}N_4O$ 284,1637; found 284.1643.

EXAMPLE 6

(endo-N-(9-Methyl-9-azabicyclo[3.3.1]nonan-3-yl)-6-chloroimidazo[1,2-a]pyridine-8-carboxamide dihydrochloride)

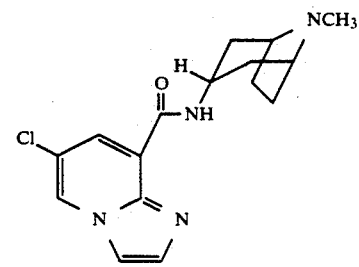

Procedure

The compound of example C (233 mg, 0.001 mol) and 1,1'-carbonyldiimidazole (178 mg, 0.001 mol) were suspended in DMF (5 ml), and the mixture was stirred for one hour before adding endo-N-9-methyl-9-azabicyclo[3.3.1]-nonane-3-amine (154 mg, 0.0011 moles). The mixture was stirred for 18 hours. Tlc (30% EtOH/CH$_2$Cl$_2$/1/10% NH$_4$OH) indicated that the reaction was complete. Concentration afforded a residue which was suspended in water and the pH adjusted to 11 with K$_2$CO$_3$. The solid was filtered and purified by radial chromatography [(2 mm plate), gradient elution 25% to 75% i-PrOH/CH$_2$Cl$_2$/1/10% NH$_4$OH]. Two components were collected. The desired product was found in the second-eluted component. Concentration afforded a residue which was converted to the hydrochloride salt by dissolving the residue in iPrOH then acetone and passing HCl gas over the solution. The solid wa filtered, washed with i-PrOH then acetone and dried in a vacuum desicator to yield 168 mg (32%) of the title compound.

| Elements | Calc | Found | |
|---|---|---|---|
| Carbon | 45.57 | 45.36 | $C_{17}H_{21}ClN_4O*2.5$ HCl*2.5 H$_2$O*acetone |
| Hydrogen | 6.60 | 6.68 | |
| Nitrogen | 10.63 | 10.61 | MW 527.106 |
| Chlorine | 23.54 | 23.67 | |

EXAMPLE 7

(N-(1-Azabicyclo[2.2.2]octan-3-yl)-6-chloroimidazo[1,2-a]pyridine-8-carboxamide dihydrochloride)

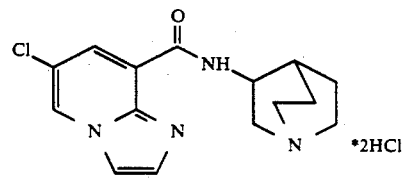

*2HCl

Procedure

Using the compound of example C (233 mg, 0.001 moles), 1,1'-carbonyldiimidazole (241 mg, 0.0015 moles), and 3-aminoquinuclidine dihydrochloride (280 mg, 0.002 moles) in DMF (5 ml) the coupling was performed as discribed in example 3.

The residue was partitioned between dilute K₂CO₃ and CH₂Cl₂. The organic layer was separated, dried over MgSO₄ and concentrated to afford to an oil. The oil was purifed by silica gel chromatography [gradient elution with 20% to 100% iPrOH/CH₂Cl₂/1/10% NH₄OH]. The fractions containing the desired product were combined and concentrated to an oil which crystallized. The solid residue was converted to the hydrochloride salt by dissolving the residue in iPrOH and passing HCl gas over the solution. The solid was filtered, washed with iPrOH and dried in a vacuum desicator to yield 221 mg (56%) of the title compound.

| Elements | Calc | Found | |
|---|---|---|---|
| Carbon | 45.55 | 45.95 | $C_{15}H_{17}ClN_4O \cdot 2\ HCl \cdot H_2O$ |
| Hydrogen | 5.35 | 5.13 | |
| Nitrogen | 14.16 | 14.45 | MW 395.72 |
| Chlorine | 26.88 | 27.11 | |

EXAMPLE 8

(N-(1-Azabicyclo[2.2.2]octan-3-yl)imidazo[1,2-a]pyridine-8-carboxamide, dihydrochloride)

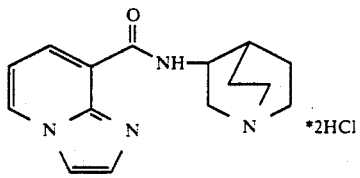

Procedure

Employing the compound of example D (1.98 g, 0.01 mol), SOCl₂ (2.3 g/1.4 ml, 0.02 mol), 3-aminoquinuclidine dihydrochloride (200 mg, 0.01 mol), and Et₃N (4.0 g/5.6 ml, 0.04 mol) dissolved in CHCl₃/DMF (25 ml/3 drops) the same procedure as described in example 1 was used. After workup 2.2 mg (59%) of the title compound was isolated, m.p. 222° C. (softens); 241°–245° C. (decomposes).

| Elements | Calc | Found | |
|---|---|---|---|
| Carbon | 50.88 | 50.73 | $C_{15}H_{218}N_{46}O \cdot 2HCl \cdot 0.25H_2O \cdot 0.75iPrOH$ |
| Hydrogen | 6.37 | 6.06 | |
| Nitrogen | 15.07 | 15.40 | MW 371.79 |
| Chlorine | 19.07 | 18.83 | |

EXAMPLE 9

((±)-endo-N-(Hexahydro-1H-2,5β-methano-3aα,6aα-cyclopenta[c]pyrrol-4α-yl)-6-chloroimidazo[1,2-a]pyridine-8-carboxamide, monohydrochloride)

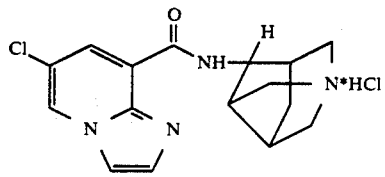

Procedure

The compound of example C (115 mg, 0.0005 mol) and 1,1'-carbonyldiimidazole (86 mg, 0.000525 mol) were suspended in DMF (2.5 ml), and the mixture was stirred for one hour before adding (±)-endo-N-hexahydro-1H-2,5β-methano-3aα,6aα-cyclopenta[c]pyrrol-4α-amine [U.S. patent application Ser. No. 07/515,391] (69 mg, 0.0005 mol). A solid precipitated from solution. The mixture was stirred for an additional hour. The solid was filtered, washed with acetone, and dried to yield 97 mg (52%) of the title compound.

| Elements | Calc | Found | |
|---|---|---|---|
| Carbon | 51.76 | 51.81 | $C_{16}H_{17}ClN_4O \cdot HCl \cdot H_2O$ |
| Hydrogen | 5.43 | 5.24 | |
| Nitrogen | 15.09 | 15.27 | MW 371.27 |
| Chlorine | 19.10 | 19.47 | |

EXAMPLE 10

((±)-endo-N-(Hexahydro-1H-2,5β-methano-3aα,6aα-cyclopenta[c]pyrrol-4α-yl)imidazo[1,2-a]pyridine-8-carboxamide, hydrochloride)

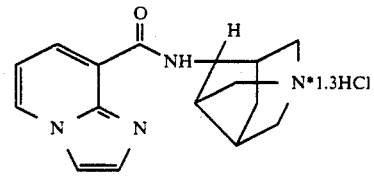

Procedure

The compound of example D (53 mg, 0.00027 mol) and 1,1'-carbonyldiimidazole (43 mg, 0.00027 mol) were suspended in DMF (2 ml), and the suspension was stirred for 4.5 h. (±)-Endo-N-hexahydro-1H-2,5β-methano-3aα,6aα-cyclopenta[c]pyrrol-4α-amine was added and the mixture was stirred for 16 h. The mixture was diluted with EtOAc and the solid filtered to afford (46 mg, 58%) the title compound.

| Elements | Calc | Found | |
|---|---|---|---|
| Carbon | 58.28 | 58.17 | $C_{16}H_{18}N_4O \cdot 1.3HCl$ |
| Hydrogen | 5.90 | 5.97 | |
| Nitrogen | 16.99 | 17.04 | MW 329.54 |

MS calcd for $C_{16}H_{218}N_4O$ 282.1480; found 282.1472.

EXAMPLE 11

(exo-N-(1-azatricyclo[3.3.1.1³,⁷]decan-4-yl)-6-chloroimidazo[1,2-a]pyridine-8-carboxamide, monohydrochloride)

-continued

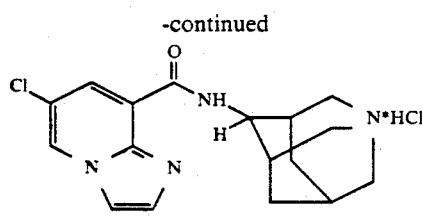

Procedure

The compound of example C (150 mg, 0.00064 mol) and 1,1'-carbonyldiimidazole (104 mg, 0.00064 mol) were suspended in DMF (1 ml), and the suspension was stirred for 2 h. A solution of exo-N-(1-azatricyclo[3.3.1.1$^{3,7}$]decane-4-amine in DMF (1 ml) was added and the mixture was stirred for 16 h. The mixture was diluted with EtOAc (4 ml). The solid was filtered to afford 226 mg of a solid which was recrystallized from MeOH to yield (139 mg, 59%) the title compound.

| Elements | Calc | Found | |
|---|---|---|---|
| Carbon | 55.60 | 55.20 | $C_{17}H_{19}ClN_4O$*1HCl |
| Hydrogen | 5.49 | 5.51 | |
| Nitrogen | 15.41 | 15.26 | MW 367.26 |
| Chlorine | 19.31 | 19.59 | |

EXAMPLE 12

(N-[2-(Diethylamino)ethyl]imidazo[1,2-a]pyridine-8-carboxamide)

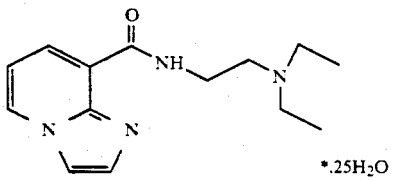

*.25H$_2$O

Procedure

Employing the compound of example D (1.98 g, 0.01 mol), SOCl$_2$ (2.3 g/1.4 ml, 0.02 mol), N,N-diethylenediamine (1.27 g, 0.011 mol), and Et$_3$N (2.0 g/2.8 ml, 0.02 mol) dissolved in CHCl$_3$/DMF (25 ml/3 drops), the same procedure as described in example 1 was used. After workup 610 mg (23%) of the title compound was isolated as an oil.

| Element | Calc | Found | |
|---|---|---|---|
| Carbon | 63.49 | 63.54 | $C_{14}H_{20}N_4O$*.25H$_2$O |
| Hydrogen | 7.80 | 7.55 | |
| Nitrogen | 21.16 | 20.99 | MW 264.83 |

EXAMPLE 13

(Cis-N-[[(4-Fluorophenoxy)propyl]-3-methoxy-4-piperidinylamine]imidazo[1,2-a]pyridine-8-carboxamide)

-continued

*2.4HCl

Procedure

Employing the compound of example D (1.98 g, 0.01 mol), SOCl$_2$ (2.3 g/1.4 ml, 0.02 mol), cis-1-[3-(4-fluorophenoxy)propyl]-3-methoxy-4-pipendinylamne (3.1 g, 0.011 mol), and Et$_3$N (3.5 g/3.84 ml, 0.035 mol) dissolved in CHCl$_3$/DMF (25 ml/3 drops), the same procedure as described in example 1 was used. After workup 2.29 mg (42%) of the title compound was isolated.

| Elements | Calc | Found | |
|---|---|---|---|
| Carbon | 50.64 | 50.74 | $C_{23}H_{29}FN_4O_3$*2.4HCl*1.75H$_2$O |
| Hydrogen | 6.08 | 5.69 | |
| Nitrogen | 10.27 | 10.44 | MW 545.53 |
| Chlorine | 15.60 | 15.44 | |

EXAMPLE 14

(N-[1-(Phenylmethyl)-4-piperidinyl]imidazo[1,2-a]pyridine-8-carboxamide, dihydrochloride)

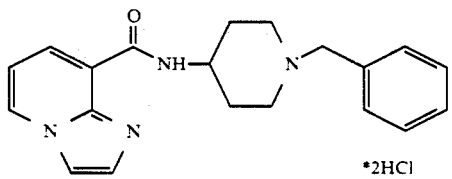

*2HCl

Procedure

Employing the compound of example D (1.98 g, 0.01 moles), SOCl$_2$ (2.3 g/1.4 ml, 0.02 mol), 4-amino-1-benzylpiperidine (2.0 g, 0.011 mol), and Et$_3$N (3.5 g/4.89 ml, 0.035 mol) dissolved in CHCl$_3$/DMF (25 ml/3 drops), the same procedure as described in example 1 was used. After workup 3.1 g (72%) of the title compound was isolated, m.p. 290°–291° C. (decomposes).

| Elements | Calc | Found | |
|---|---|---|---|
| Carbon | 56.01 | 56.32 | $C_{20}H_{22}N_4O_3$*2 HCl*.5H$_2$O |
| Hydrogen | 5.99 | 5.94 | |
| Nitrogen | 13.06 | 12.67 | MW 383.92 |
| Chlorine | 16.53 | 16.54 | |

EXAMPLE 15

((±-endo-N-(Hexahydro-1H-2,5β-methane-3aα,6aα-cyclopenta[c]pyrrol-4aα-yl)-3-ethylindolizine-1-carboxamide monohydrochloride)

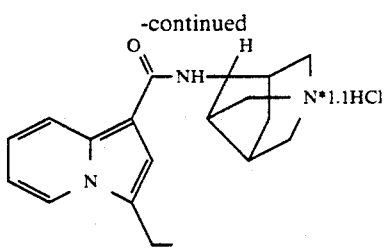

Procedure

3-Ethylindolizine-1-carboxylic acid (76.7 mg, 0.000405 mol) [prepration described by Bermudez et al. in Journal of Medicinal Chemistry (1990)33:1928] and 1,1'-carbonyldiimidazole (65.7 mg, 0.000405 mol) were suspended in DMF (5 ml) and the mixture was stirred for 4 h. (±)-Endo-N-(Hexahydro-1H-2,5β-methano-3aα,6aα-cyclopenta[c]pyrrol-4α-amine (56 mg, 0.000405 mol) in DMF (1 ml) was added and the mixture stirred an additional 22 h. An additional premixed portion of 3-ethylindolizine-1-carboxylic acid (38 mg, 0.20 mmol) and 1,1'-carbonyldiimidazole (33 mg, 0.20 mmol) in DMF (1 ml) was added. This mixture was stirred for an additional 16 h. The reaction mixture was concentrated in vacuo to give a residue which was treated with 20% $K_2CO_3$ (1 ml) and extracted with $CHCl_3$ (3X). The combined extracts were washed with water and brine and dried over $Na_2SO_4$. Concentration in vacuo gave 74 mg of an oil which was chromatographed on silica gel eluting with 3/97 $MeOH(NH_3)/CHCl_3$ to give the desired amide (21.4 mg, 17%) as the free base. The free base was converted to the hydrochloride salt by dissolving in HCl/MeOH [prepared from acetyl chloride (4.9 μl, 0.069 mmol) and MeOH (1 ml)]. Concentration in vacuo gave the desired hydrochloride salt (24.2 mg) as a solid.

| Elements | Calc | Found | | |
|---|---|---|---|---|
| Carbon | 60.61 | 60.55 | $C_{19}H_{23}N_3O\cdot1.1HCl\cdot1.5H_2O$ | |
| Hydrogen | 7.25 | 6.80 | | |
| Nitrogen | 11.16 | 11.06 | MW 376.31 | |

MS calcd for $C_{19}H_{23}N_3O$:309.1841; found 309.1845.

EXAMPLE 16

((±)-endo-N-(Hexahydro-1H-2,5β-methano-3aα,6aα-cyclopenta[c]pyrrol-4α-yl)-3-ethylimidazo[1,5-a]pyridine-1-carboxamide, monohydrochloride)

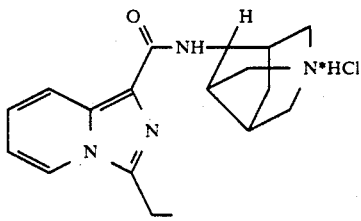

Procedure

3-Ethylimidazo[1,5-a]pyridine-1-carboxylic acid (72.9 mg, 0.00038 mol) [prepration described by Bermudez et al. in Journal of Medicinal Chemistry, (1990)33, 1928] and 1,1'-carbonyldi-imidazole (62 mg, 0.00038 mol) were suspended in DMF (0.5 ml) and the mixture was stirred for 4 h. (±)-Endo-N-(Hexahydro-1H-2,5β-methano-3aα,6aα-cyclopenta[c]pyrrol-4α-amine (53 mg, 0.00038 mol) in DMF (1 ml) was added and the mixture stirred an additional 40 h. The reaction mixture was concentrated in vacuo to give a residue which was treated with 20% $K_2CO_3$ (1 ml) and extracted with $CHCl_3$ (3X). The combined extracts were washed with water and brine and dried over $Na_2SO_4$. Concentration in vacuo gave 127 mg of a solid which was chromatographed on silica gel eluting with 2/98 $MeOH(NH_3)/CHCl_3$ to give the desired amide (43 mg, 36%) as the free base. The free base was converted to the hydrochloride salt by dissolving in NCl/MeOH [prepared from acetyl chloride (8.8 μl, 0.00014 mol) and MeOH (1 ml)]. Addition of this methanolic solution to diethyl ether (75 ml) and filtration gave the title compound as the hydrochloride salt (39 mg).

MS calcd for $C_{18}H_{22}N_4O$:310.1793; found 310.1791.

EXAMPLE 17

(R-N-(1-Azabicyclo[2.2.2]octan-3-yl)imidazo[1,2-a]pyridine-2-carboxamide dihydrochloride)

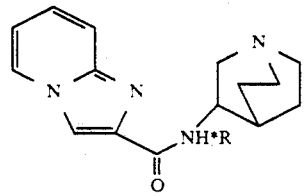

Procedure

The compound of example E (216 mg, 0.001 mol) and 1,1'-carbonyldiimidazole (178 mg, 0.001 mol) were suspended in DMF (5 ml), and the mixture was stirred for 1 h before adding R-3-aminoquinuclidine dihydrochloride (200 mg, 0.001 mol), synthesized using the procedure in European Patent #0280 603. The mixture was stirred for 18 hours. Tlc (30% $EtOH/CH_2Cl_2/1/10\%$ $NH_4OH$) indicated that the reaction was complete. Concentration afforded a residue which was suspended in water and the pH adjusted to 11 with $K_2CO_3$. The solid which formed was filtered and purified by radial chromatography [(2 mm plate), gradient elution 25% to 75% i-PrOH/$CH_2Cl_2$/1/10% $NH_4OH$] to afford a residue which was converted to the hydrochloride salt by dissolving the residue in iPrOH and passing HCl gas over the solution. The solid was filtered, washed with iPrOH and dried in a vacuum desicator to yield 169 mg (47%) of the title compound.

| Elements | Calc | Found | |
|---|---|---|---|
| Carbon | 51.61 | 51.83 | $C_{15}H_{18}N_4O\cdot2.15HCl\cdot0.1H_2O\cdot0.15iPrOH$ |
| Hydrogen | 6.04 | 6.06 | |
| Nitrogen | 15.58 | 15.44 | MW 359.54 |
| Chlorine | 21.20 | 21.11 | |

EXAMPLE 18

(S-N-(1-Azabicyclo[2.2.2]octan-3-yl)imidazo[1,2-a]pyridine-2-carboxamide dihydrochloride)

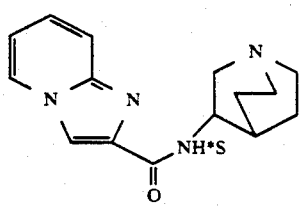

Procedure

Employing the compound of example E (216 mg, 0.001 mol), 1,1'-carbonyldiimidazole (178 mg, 0.001 mol) DMF (5 ml), S-3-aminoquinuclidine dihydrochloride (200 mg, 0.001 mol) [synthesized using the procedure in European Patent #0 280 603], the same procedure described in example 17 was used to afford the title compound (182 mg, 50%).

| Elements | Calc | Found | |
|----------|------|-------|---|
| Carbon | 51.18 | 51.53 | $C_{15}H_{18}N_4O * 2.1HCl * 0.4H_2O * 0.2iPrOH$ |
| Hydrogen | 6.19 | 6.02 | |
| Nitrogen | 15.30 | 15.19 | MW 366.13 |
| Chlorine | 20.33 | 20.09 | |

The compounds herein exhibit 5-HT3 antagonism. 5-HT3 antagonism can be determined by the radioligand receptor binding assay as described herein and in the in vivo Bezold-Jarisch reflex procedure.

Serotonin (5-HT$_3$)

Procedure:

GR65630 binds to the 5-HT$_3$ receptor. Brain cortices are obtained from male rats and a membrane fraction prepared by standard techniques. 0.04 mg of membrane prep is incubated with 0.2 nM [$^3$H]-GR656630 for 60 minutes at 22° C. Non-specific binding is estimated in the presence of 1 uM ICS 205-930. Membranes are filtered and washed 3 times and the filters are counted to determine [3H]-GR65630 specifically bound.*

*Literature Reference:
Kilpatrick GJ, Jones BJ and Tyers MB. Identification and distribution of 5-HT$_3$ receptors in rat brain using radioligand binding. Nature. 330:746–748, 1987

Results:

Kd = 2.46 nM

Bmax = 154 fmol/mg protein

% Specific Binding: 70

| Effect of Reference Compounds on [H]-GR65630 Bound (0.2 nM) | | | |
|---|---|---|---|
| Compound | IC$_{50}$ | Ki | Hill Coefficient |
| Quipazine | 0.5 nM | 0.18 nM | 0.86 |
| ICS 205-930 | 0.2 nM | 0.51 nM | 1.0 |
| 5-HT | 122 nM | 0.39 uM | 1.0 |
| RU24969 | 320 nM | 1.85 uM | 1.0 |
| Zacopride | 0.55 nM | 0.18 nM | 0.86 |

Bezold-Jarisch Reflex

The test sample is administered i.p. (mg/kg) to a group of 3 mice. Thirty minutes later, a 5-HT (0.25 mg/kg i.v.)-induced bradycardia is recorded in pentobarbital anesthetized animals. A greater than 50 percent (>50) reduction in the bradycardic response relative to vehicle-treated control mice is considered significant.

| REFERENCE AGENTS: | Minimum Effective Dose (MED), mg/kg |
|---|---|
| BRL-43694 | 0.05 |
| cisapride | 5 |
| cyproheptadine | 5 |
| domperidone | >10 |
| GR-38032 | 0.5 |
| ketanserin | >10 |
| mecamylamine | 2.5 |
| methysergide | >10 |
| metoclopramide | 5 |
| scopolamine | 2.5 |

This method has been described by Saxena, P. R. and Lawang, A., Arch. Int. Pharmacodyn., 277:235–252, 1985.

| TEST PROCEDURE | |
|---|---|
| 5-HT3 BINDING: | BEZOLD JARISCH REFLEX (Mice): |

| Example No. | NG10B-15 Cells IC50 | % Inhibition @ Dose (IP) |
|---|---|---|
| 1 | 6.3 nM | 87% @ 10 |
|   | 274 nM | 73% @ 3 |
|   | Ki = 137 nM | 68% @ 1 |
|   |   | N @ 0.3 |
| 2 |   | 53% @ 10 |
|   |   | 1% @ 5 |
| 3 | 19.34 nM |   |
|   | 99 nM |   |
|   | Ki = 50 nM | — |
| 4 | 500 nM | 82% @ 10 |
|   | 831 nM | 2% @ 3 |
|   | Ki = 416 nM |   |
| 5 | 475 nM | 80% @ 10 |
|   | 628 nM | N @ 3 |
|   | Ki = 314 nM |   |
| 6 | 2.36 nM |   |
|   | 9.8 nM |   |
|   | Ki = 4.9 nM |   |
| 7 | 17.5 nM |   |
|   | 23 nM |   |
|   | Ki = 12 nM |   |
| 8 | 70 nM | 100% @ 10 |
|   |   | 95% @ 5 |
|   |   | 88% @ 2.5 |
|   |   | 82% @ 0.5 |
|   |   | N @ 0.25 |
| 9 | 16 nM |   |
|   | 127 nM |   |
|   | Ki = 64 nM |   |
| 10 | 200 nM | 81% @ 10 |
|   | 243 nM | N @ 3 |
|   | Ki = 122 nM |   |
| 11 | >100 nM |   |
| 12 | 17 nM | N @ 10 |
| 13 | 23% @ 100 nM | 23% @ 10 |
| 14 |   | N @ 10 |
| 15 | 26.33 nM |   |
| 16 | 30 nM |   |

Also embraced within this invention is a class of pharmaceutical compositions comprising one or more of the described compounds in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight, may be appropriate.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:
1. A compound of the formula

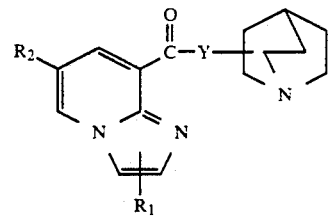

the stereoisomers and pharmaceutically acceptable salts thereof, wherein $R_1$ is H or $C_{1-6}$ alkyl and $R_2$ is H or halogen; and Y represents NH or O.

2. A compound of claim 1 wherein $R_1$ is H and $R_2$ is H or halo; and Y is NH.

3. A compound of claim 2 wherein $R_2$ is chloro.

4. The compound of claim 1 which is N-(1-Azabicyclo-octan-3-yl)-6-chloroimidazo-pyridine-8-carboxamide dihydrochloride.

5. The compound of claim 1 which is N-(1-Azabicyclo-octan-3-yl)imidazo-pyridine-8-carboxamide, dihydrochloride.

6. The compound of claim 1 which is R-N-(1-Azabicyclo-octan-3-yl)imidazo-pyridine-2-carboxamide dihydrochloride.

7. The compound of claim 1 which is S-N-(1-Azabicyclo-octan-3-yl)imidazo-pyridine-2-carboxamide dihydrochloride.

8. A pharmaceutical composition for the treatment of anxiety, psychoses, depression, substance abuse, cognitive disorders, gastrointestinal motility disturbances or conditions responsive to 5-HT$_3$ antagonists comprising a therapeutically effective amount of a compound of claim 1 and a pharmaceutically acceptable carrier or diluent.

9. A pharmaceutical composition of claim 8 wherein $R_1$ is H and $R_2$ is H or halo; and
Y is NH.

10. A pharmaceutical composition of claim 9 wherein $R_2$ is chloro.

11. The pharmaceutical composition of claim 8 wherein the compound is (N-(1-Azabicyclo-octan-3-yl)-6-chloroimidazo-pyridine-8-carboxamide dihydrochloride).

12. The pharmaceutical composition of claim 8 wherein the compound is (N-(1-Azabicyclo-octan-3-yl)imidazo-pyridine-8-carboxamide, dihydrochloride).

13. The pharmaceutical composition of claim 8 wherein the compound is (R-N-(1-Azabicyclo-octan-3-yl)imidazo-pyridine-2-carboxamide dihydrochloride).

14. The pharmaceutical composition of claim 8 wherein the compound is (S-N-(1-Azabicyclo-octan-3-yl)imidazo-pyridine-2-carboxamide dihydrochloride).

15. The method of treating anxiety, psychoses, depression or gastrointestinal motility disturbances comprising administering to a subject in need of such treatment a therapeutically effective amount of a compound of claim 1.

16. The method of claim 15 wherein $R_1$ is H and $R_2$ is H or halo; and
Y is NH.

17. The method of claim 16 wherein $R_2$ is chloro.

18. The method of claim 15 wherein the compound is (N-(1-Azabicyclo-octan-3-yl)-6-chloroimidazo-pyridine-8-carboxamide dihydrochloride).

19. The method of claim 15 wherein the compound is (N-(1-Azabicyclo-octan-3-yl)imidazo-pyridine-8-carboxamide, dihydrochloride).

20. The method of claim 15 wherein the compound is (R-N-(1-Azabicyclo-octan-3-yl)imidazo-pyridine-2-carboxamide dihydrochloride).

21. The method of claim 15 wherein the compound is (S-N-(1-Azabicyclo-octan-3-yl)imidazo-pyridine-2-carboxamide dihydrochloride).

22. The method of treating a condition responsive to 5-$HT_3$ antagonism comprising administering to a subject in need of such treatment a therapeutically effective amount of a compound of claim 1.

23. The method of claim 22 wherein $R_1$ is H and $R_2$ is H or halo; and
Y is NH.

24. The method of claim 23 wherein $R_2$ is chloro.

* * * * *

UNITED STATES PATENT AND TRADEMARK OFFICE
CERTIFICATE OF CORRECTION

PATENT NO. : 5,260,303    Page 1 of 2
DATED : November 9, 1993
INVENTOR(S) : Becker, et al.

It is certified that error appears in the above-indentified patent and that said Letters Patent is hereby corrected as shown below:

Column 1, line 28, reading "n U.K." should read -- in U.K. --.

Column 5, line 16, reading "$\geqq$" should read -- $\geq$ --.

Column 19, line 49, reading "$N_{46}O$" should read -- $N_4O$ --.

Column 21, line 57, reading "Element" should read -- Elements --.

Column 21, line 66, reading "(Cis-N-[[(4-" should read -- (Cis-N-[[3-(4- --.

Column 22, line 65, reading "(($\pm$-endo-" should read -- (($\pm$)-endo- --.

Column 28, line 57, reading "The method" should read -- A method --.

UNITED STATES PATENT AND TRADEMARK OFFICE
CERTIFICATE OF CORRECTION

PATENT NO. : 5,260,303
DATED : November 9, 1993
INVENTOR(S) : Becker, et al.

It is certified that error appears in the above-indentified patent and that said Letters Patent is hereby corrected as shown below:

At Column 28, lines 18, 44 and 67, all occurrences reading "N-(1-Azabicyclo-octan-3-yl)-6-chloroimidazo" should read -- N-(1-Azabicyclo[2.2.2]octan-3-yl)-6-chloroimidazo[1,2-a] --.

At Column 28, lines 21, 24, 27, 48, 51, 54, and Column 29, lines 2, 5 and 8, all occurrences reading "N-(1-Azabicyclo-octan-3-yl)imidazo" should read -- N-(1-Azabicyclo[2.2.2]octan-3-yl)imidazo[1,2-a] --.

Signed and Sealed this

Sixteenth Day of May, 1995

Attest:

BRUCE LEHMAN

*Attesting Officer*   *Commissioner of Patents and Trademarks*